(12) United States Patent
Shieh et al.

(10) Patent No.: US 6,538,455 B2
(45) Date of Patent: Mar. 25, 2003

(54) COUPLING FOR A REFLECTIVITY-MEASURING DEVICE

(75) Inventors: Shiao-Ping Shieh, Hsinchu Hsien (TW); Hsien-Hsiang Lin, Kaohsiung Hsien (TW); Thanku Shieh, Kaohsiung Hsien (TW); Wen-Chien Wu, Hsinchu Hsien (TW)

(73) Assignee: Mosel Vitelic Inc., Hsinchu (TW)

( * ) Notice: Subject to any disclaimer, the term of this patent is extended or adjusted under 35 U.S.C. 154(b) by 0 days.

(21) Appl. No.: 09/864,372

(22) Filed: May 25, 2001

(65) Prior Publication Data

US 2002/0079907 A1 Jun. 27, 2002

(30) Foreign Application Priority Data

Dec. 21, 2000 (TW) ...................... 89222226 U

(51) Int. Cl.⁷ .............................. G01R 27/04; F16H 1/24
(52) U.S. Cl. .................... 324/644; 74/424.85
(58) Field of Search ................. 324/644, 632, 324/772; 310/80, 114, 87; 438/14, 72, 8; 204/298.01, 192.27; 407/307; 74/89.23, 424.85

(56) References Cited

U.S. PATENT DOCUMENTS 5,319,991 A * 6/1994 Pierrat .................... 192/141
6,075,299 A * 6/2000 Miyazaki et al. ........... 174/51

* cited by examiner

*Primary Examiner*—N. Le
*Assistant Examiner*—James Kerveros
(74) *Attorney, Agent, or Firm*—Birch, Stewart, Kolasch & Birch, LLP

(57) ABSTRACT

A coupling for a reflectivity-measuring device connects a first shaft of a reflectivity-measuring device with a second shaft of a motor. The first shaft inserts into a first hole of a main portion of the coupling, and the second shaft inserts into a second hole of the main portion. The main portion further comprises a third hole communicating with the first hole, a fourth hole communicating with the second hole; a first non-skid member and a second non-skid member. The first non-skid member inserts into the third hole and abuts the first shaft located inside the first hole. The second non-skid member inserts into the fourth hole and abuts the second shaft located inside the second hole.

6 Claims, 4 Drawing Sheets

COUPLING FOR A REFLECTIVITY-MEASURING DEVICE

BACKGROUND OF THE INVENTION

1. Field of the Invention

The invention relates to a coupling; in particular, the invention relates to a coupling that can prevent a shaft of a reflectivity-measuring device from skidding.

2. Description of the Related Art

In the semiconductor manufacturing process, there is a process to electroplate a film on a wafer. After such a process is completed, a reflectivity-measuring device measures the thickness of the film.

Referring to FIG. 1, the reflectivity-measuring device 30 connects with a motor 20 by a coupling 10. A first shaft 31 of the reflectivity-measuring device 30 and a second shaft 21 of the motor 20 are inserted into the coupling 10 separately. Therefore, the motor 20 drives the reflectivity-measuring device 30 through the coupling 10 in order to focus.

Referring to FIG. 2a, FIG. 2b and FIG. 2c, the coupling 10 comprises a main portion 11 and plural screws 18. A first hole 12 and a second hole 13 are formed on both end surfaces of the main portion 11. The first hole 12 is used for the first shaft 31 inserting therein, and the second hole 13 is used for the second shaft 21 inserting therein. A first screw hole 14 and a second screw hole 15 are formed on the circumference surface of the main portion 11. The first screw hole 14 and the second screw hole 15 are used for the screws 18 inserting therein. Furthermore, a first slot 16, communicating with the first hole 12 and the first screw hole 14, is formed on the main portion 11. A second slot 17, communicating with the second hole 13 and the second screw hole 15, is formed on the main portion 11. By means of the deposition of the first slot 16 and the second slot 17, the first hole 12 and the second hole 13 have a larger space before the first shaft 31 and the second shaft 21 are inserted into the first hole 12 and the second hole 13. After the first shaft 31 and the second shaft 21 are put in the first hole 12 and the second hole 13 separately, the screws 18 are screwed to the first screw hole 14 and the second screw hole 15 separately in order to decrease the gaps of the first slot 16 and the second slot 17. As a result, the sizes of the first hole 12 and the second hole 13 become smaller, the first shaft 31 and the second shaft 21 are locked inside the main portion 11.

However, since the diameters of the first shaft 31 and the second shaft 21 are extremely small, the screws 18 cannot lock the first shaft 31 and the second shaft 21 inside the main portion 11 completely. Furthermore, the output of the first shaft 31 is usually large, the skid between the first shaft 31 and the main portion 11 easily occurs. Hence, during the focus of the reflectivity-measuring device 30, errors also easily occur.

SUMMARY OF THE INVENTION

In view of the disadvantages of the aforementioned conventional coupling, the invention provides a coupling that can prevent a shaft of a reflectivity-measuring device from skidding.

Accordingly, the invention provides a coupling for connecting a reflectivity-measuring device with a motor. The reflectivity-measuring device has a first shaft, and the motor has a second shaft. The coupling comprises a main portion having a first hole and a second hole. The first hole is used for the first shaft inserting therein, and the second hole is used for the second shaft inserting therein. The main portion further comprises a third hole, communicating with the first hole, and a first non-skid member, inserting into the third hole and abutting the first shaft located inside the first hole.

Furthermore, the main portion further comprises a fourth hole, communicating with the second hole, and a second non-skid member, inserting into the fourth hole and abutting the second shaft located inside the second hole.

Furthermore, the number of the third hole is not less than one, the number of the first non-skid member is not less than one, the number of the fourth hole is not less than one, and the number of the second non-skid member is not less than one.

Furthermore, the invention provides a coupling for a reflectivity-measuring device. The reflectivity-measuring device has a first shaft. The coupling comprises a main portion having a first hole. The first hole is used for the first shaft inserting therein. The main portion further comprises a third hole, communicating with the first hole, and a first non-skid member, inserted into the third hole and abutting the first shaft located inside the first hole.

BRIEF DESCRIPTION OF THE DRAWINGS

The invention is hereinafter described in detail by reference to the accompanying drawings in which.

DETAILED DESCRIPTION OF THE INVENTION

Figure 1:
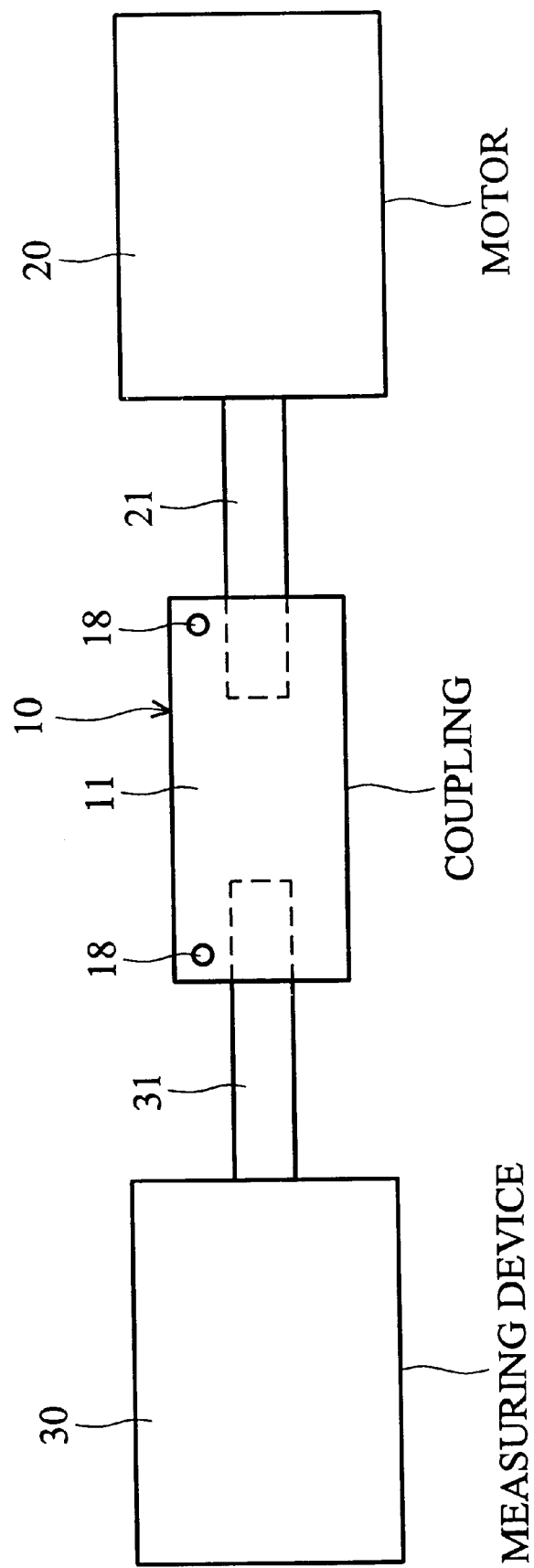
FIG. 1 is a schematic view depicting a conventional coupling for connecting a reflectivity-measuring device and a motor.
Figure 2C:
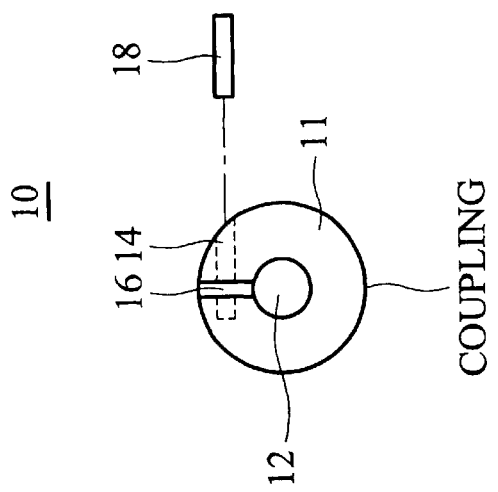
FIG. 2c is a side view depicting the conventional coupling.
Figure 2B:
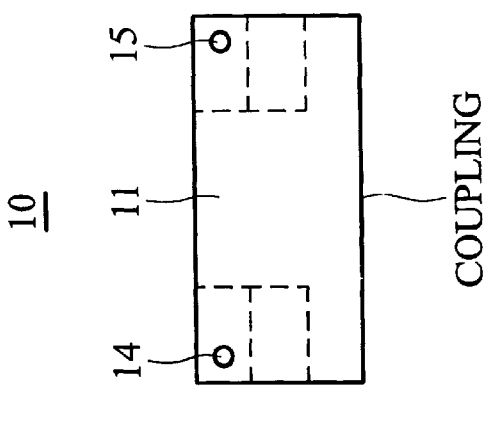
FIG. 2b is a front view depicting the conventional coupling.
Figure 2A:
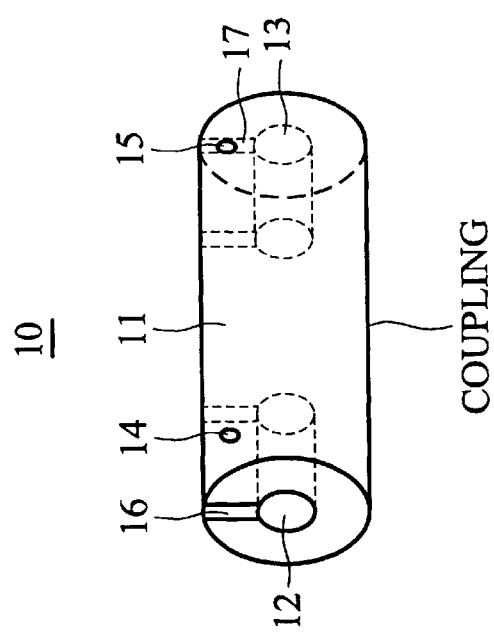
FIG. 2a is a perspective view depicting the conventional coupling.
Figures 3A, 3B, 3C:
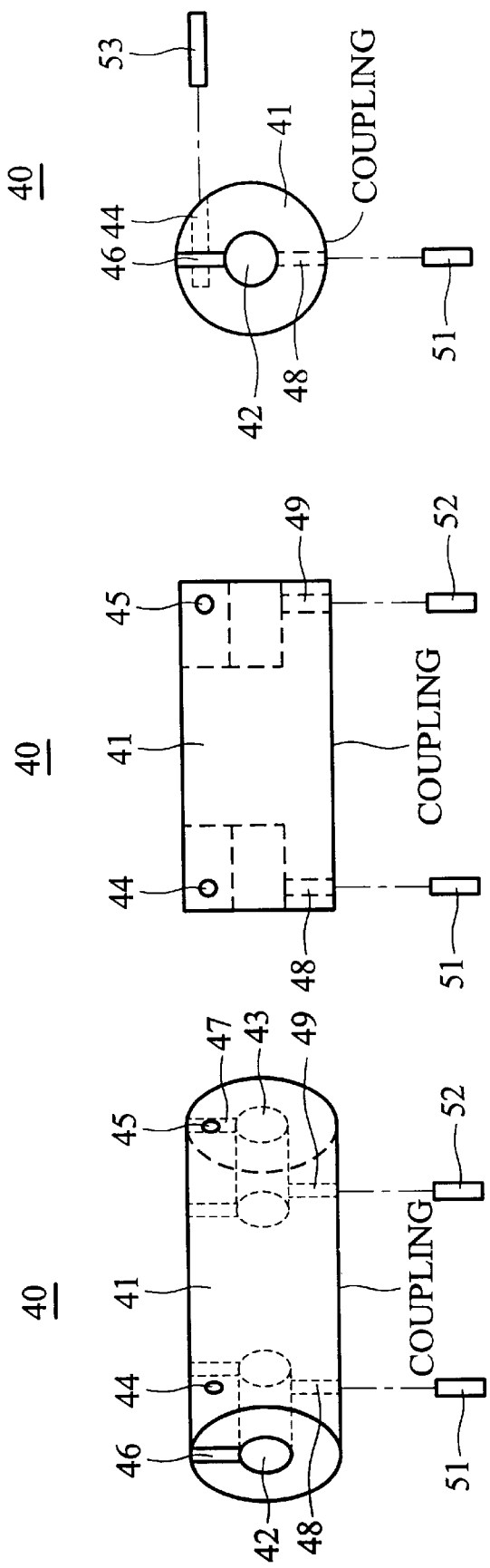
FIG. 3a is a perspective view depicting a coupling of this invention.
FIG. 3b is a front view depicting the coupling of this invention.
FIG. 3c is a side view depicting the coupling of this invention.

Referring to FIG. 3a, FIG. 3b and FIG. 3c, like the conventional coupling 10, the coupling 40 of this invention comprises a main portion 41 and plural screws 53. A first hole 42 and a second hole 43 are formed on both end surfaces of the main portion 41. The first hole 42 is used for the first shaft 31 shown in FIG. 4 inserting therein, and the second hole 43 is used for the second shaft 21 shown in FIG. 4 inserting therein. A first screw hole 44 and a second screw hole 45 are formed on the circumference surface of the main portion 41. The first screw hole 44 and the second screw hole 45 are used for the screws 53 inserting therein. Furthermore, a first slot 46, communicating with the first hole 42 and the first screw hole 44, is formed on the main portion 41. A second slot 47, communicating with the second hole 43 and the second screw hole 45, is formed on the main portion 41. By means of the deposition of the first slot 46 and the second slot 47, the first hole 42 and the second hole 43 have a larger space before the first shaft 31 and the second shaft 21 insert into the first hole 42 and the second hole 43. After the first shaft 31 and the second shaft 21 are put in the first hole 42 and the second hole 43 separately, the screws 53 are screwed to the first screw hole 44 and the second screw hole 45 separately in order to decrease the gaps of the first slot 46 and the second slot 47. As a result, the sizes of the first hole 42 and the second hole 43 become smaller, the first shaft 31 and the second shaft 21 are locked inside the main portion 41.

A third hole 48, communicating with the first hole 42, is formed on the circumference surface of the main portion 41. A fourth hole 49, communicating with the second hole 43, is formed on the circumference surface of the main portion 41. The coupling 40 further comprises a first non-skid member 51 and a second non-skid member 52.

After the first shaft 31 and the second shaft 21 are locked inside the main portion 41, the first non-skid member 51 is inserted into the third hole 48, while the second non-skid member 52 is inserted into the fourth hole 49. Since the third hole 48 communicates with the first hole 42, the first non-skid member 51 abuts the shaft 31 when the first non-skid member 51 is screwed to the third hole 48. Also, since the fourth hole 49 communicates with the second hole 43, the second non-skid member 52 abuts the shaft 21 when the second non-skid member 52 is screwed to the fourth hole 49.

Figure 4:
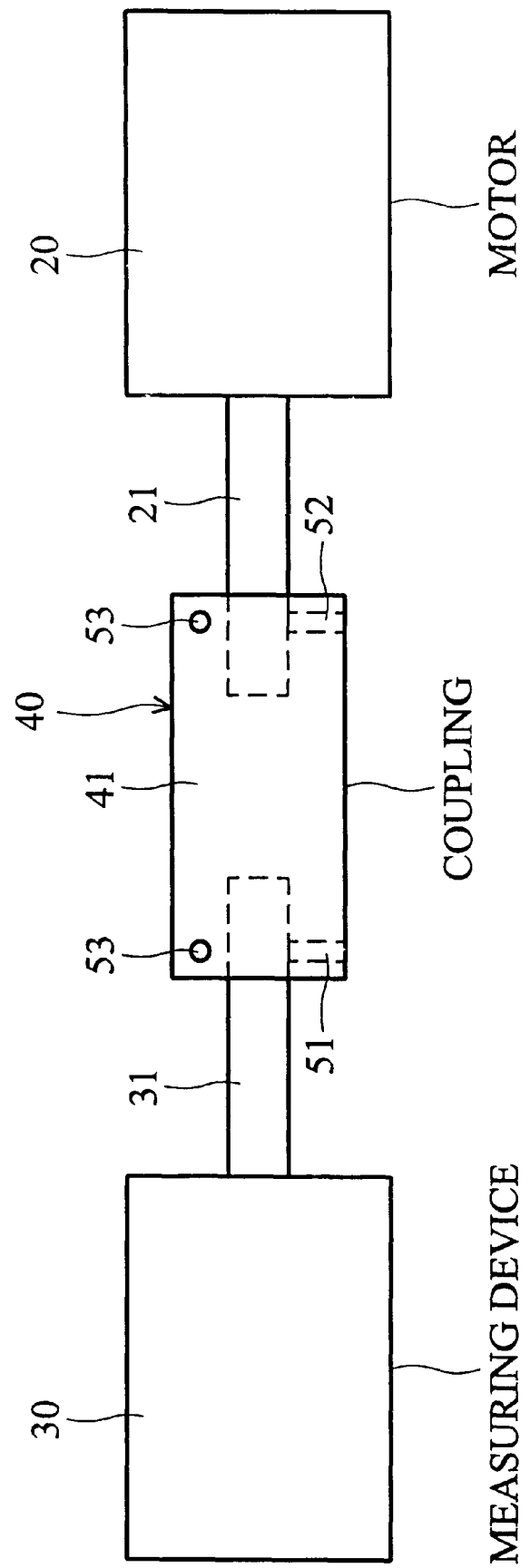
FIG. 4 is a schematic view depicting the coupling of this invention, wherein the coupling connects a reflectivity-measuring device with a motor.

As shown in FIG. 4, by means of the contact between the first non-skid member 51 and the first shaft 31, the skid of the first shaft 31 inside the coupling 40 can be avoided. Also, by means of the contact between the second non-skid member 52 and the second shaft 21, the skid of the second shaft 21 inside the coupling 40 can be avoided.

Furthermore, the contact surface between the first shaft 31 and the first non-skid member 51 is preferably to be a flat one. Also, the contact surface between the second shaft 21 and the second non-skid member 52 is preferably to be a flat one.

In addition, the number of the third hole or the fourth is not limited to one as long as the requirement of the cost is satisfied. Accordingly, the number of the first non-skid member or the second non-skid member increases.

While the invention has been particularly shown and described with reference to a preferred embodiment, it will be readily appreciated by those of ordinary skill in the art that various changes and modifications may be made without departing from the spirit and scope of the invention. It is intended that the claims be interpreted to cover the disclosed embodiment, those alternatives which have been discussed above, and all equivalents thereto.

What is claimed is:

1. A coupling for connecting a reflectivity-measuring device with a motor, wherein the reflectivity-measuring device has a first shaft, the motor has a second shaft, and the coupling comprises:

a main portion having a first hole, a second hole and a third hole, communicating with the first hole, wherein the first hole is used for the first shaft inserting therein, and the second hole is used for the second shaft inserting therein; and a first non-skid member, inserting into the third hole and abutting the first shaft located inside the first hole.

2. The coupling as claimed in claim 1, wherein the main portion further comprises a fourth hole, communicating with the second hole, and a second non-skid member, inserting into the fourth hole and abutting the second shaft located inside the second hole.

3. The coupling as claimed in claim 1, wherein the number of the third hole is not less than one, and the number of the first non-skid member is not less than one.

4. The coupling as claimed in claim 2, wherein the number of the fourth hole is not less than one, and the number of the second non-skid member is not less than one.

5. A coupling for a reflectivity measuring device, wherein the reflectivity-measuring device has a first shaft, and the coupling comprises:

a main portion having a first hole and a third hole, communicating with the first hole, wherein the first hole is used for the first shaft inserting therein; and a first non-skid member, inserted into the third hole and abutting the first shaft located inside the first hole.

6. The coupling as claimed in claim 5, wherein the number of the third hole is not less than one, and the number of the first non-skid member is not less than one.

* * * * *